(12) United States Patent
Stout

(10) Patent No.: US 6,765,122 B1
(45) Date of Patent: Jul. 20, 2004

(54) FEEDING TUBE SKIN GUARD

(76) Inventor: Cindy Kay Stout, 7890 W. Lefty Ct., Crystal River, FL (US) 34428

( * ) Notice: Subject to any disclaimer, the term of this patent is extended or adjusted under 35 U.S.C. 154(b) by 0 days.

(21) Appl. No.: 10/249,231

(22) Filed: Mar. 25, 2003

Related U.S. Application Data

(63) Continuation-in-part of application No. 09/682,254, filed on Aug. 9, 2001, now abandoned.

(51) Int. Cl.[7] .............................................. A61F 13/00
(52) U.S. Cl. .......................... 602/41; 604/174; 604/179
(58) Field of Search ................................ 604/174–180, 604/332, 338, 346, 355; 128/888, 889; 602/41, 42, 43

(56) References Cited

U.S. PATENT DOCUMENTS

| | | |
|---|---|---|
| 4,080,970 A | 3/1978 | Miller |
| 4,699,616 A | 10/1987 | Nowak et al. |
| 4,735,615 A | 4/1988 | Uddo, Jr. et al. |
| 4,865,594 A | 9/1989 | Thomas |
| 4,915,694 A | 4/1990 | Yamamoto et al. |
| 4,973,323 A | 11/1990 | Kaczmarek et al. |
| 5,207,652 A | 5/1993 | Kay |
| 5,224,935 A * | 7/1993 | Hollands ..................... 604/180 |
| 5,232,453 A | 8/1993 | Plass et al. |
| 5,242,415 A | 9/1993 | Kantrowitz et al. |
| 5,358,488 A | 10/1994 | Suriyapa |
| 5,364,367 A | 11/1994 | Banks et al. |
| 5,484,420 A | 1/1996 | Russo |
| 5,554,106 A * | 9/1996 | Layman-Spillar et al. .... 602/42 |
| 5,569,207 A | 10/1996 | Gisselberg et al. |
| 5,620,419 A | 4/1997 | Lui et al. |
| 5,620,424 A | 4/1997 | Abramson |
| 5,713,869 A | 2/1998 | Morejon |
| 5,738,661 A | 4/1998 | Larice |
| 5,764,723 A | 6/1998 | Weinberger et al. |
| 5,906,600 A | 5/1999 | Bahr |
| 5,968,000 A | 10/1999 | Harrison et al. |
| 6,071,268 A | 6/2000 | Wagner |

FOREIGN PATENT DOCUMENTS

GB          2211417 A  *  7/1989  .......... A61M/25/02

OTHER PUBLICATIONS

Hydrophilic Foam Dressings, www.wounds1.com/care/procedure20.cfm?procID=20, Jun. 15, 2001.
Dressings Polyrethane Foam BP, www.smtl.co.uk/WMPRC/DataCards/HTML/lyofoam,html, Jun. 15, 2001.
Percutaneout Gastrostomy Tube Care, www.chmcc.org/family/pep/homecare/2061, Jun. 15, 2001.
Guidelines for the Use of Enteral Nutrition, American Gastroenterological Association, www.harcourthealth.com/gastro/policy/v108n4p1280.html, Jun. 18, 2001.

(List continued on next page.)

*Primary Examiner*—Kim M. Lewis
(74) *Attorney, Agent, or Firm*—Ronald E. Smith; Smith & Hopen, P.A.

(57) ABSTRACT

A hydrophilic dressing device for use with a gastrostomy tube. The device has a disc-shaped configuration with a central opening. A radial cut extends from the central opening to a peripheral edge of the device to create a pair of opposed free ends that are releasably attachable to one another to facilitate attachment of the device around the tube. The device is positioned in overlying relation to the patient's skin to absorb leaking bodily fluids and prevent skin irritation. The core of the device is a hydrophilic material such as hydrophilic polyurethane foam. The core is covered by nylon because the open mesh structure of nylon allows the fluids to be absorbed by the core material and because nylon does not stick to the patient's skin. The device is washable in a residential washing machine and can be re-used indefinitely.

5 Claims, 2 Drawing Sheets

OTHER PUBLICATIONS

What is Gastroparesis?, National Digestive Diseases Information Clearinghouse, www.niddk.nih.gov/health/digest/pubs/gastro/gastro.htm, Jun. 18, 2001.

Tube Feeding for Children, Texas Pediatric Surgical Associates, www.pedisurg.com/_staff/Tube_Feeding.htm, Jun. 18, 2001.

Gastrojejunal (GJ) Tube Placement, Children's Hospital Boston, www.web1.tch.harvard.edu/, Jun. 18, 2001.

Gastrostomy Tube Care, Children's Hospital of Cincinnati, www.chmcc.org/family/pep/homecare/2008, Jun. 18, 2001.

The Digestive Diseases Dictionary: E–K, www.niddk.nih.gov/health/digest/pubs/dddctnry/pages/e-k.htm, Jun. 18, 2001.

* cited by examiner

FEEDING TUBE SKIN GUARD

RELATED APPLICATION

This disclosure is a continuation-in-part of a disclosure of the same title by the same inventor, filed Aug. 9, 2001, bearing Ser. No. 09/682,254 now abandoned.

BACKGROUND OF THE INVENTION

1. Field of the Invention

This invention relates, generally, to medical appliances. More particularly, it relates to a skin guard that protects the skin of a patient who receives nutrients through a gastrostomy tube.

2. Description of the Prior Art

The provision of nutritious foods to a patient through a feeding tube placed in the nose, small intestine, or stomach is known as enteral nutrition. A nasogastric or nasoenteral tube is a feeding tube placed in the nose. A jejunostomy or percutaneous endoscopic jejunostomy tube is a feeding tube placed into the small intestine. A feeding tube that extends through the skin into the stomach is called a gastrostomy or percutaneous endoscopic gastrostomy.

A feeding tube may be needed for numerous reasons. For example, a burn injury or other trauma to the head may keep a patient from swallowing comfortably. Further conditions that may require tube feedings include severe cerebral palsy, traum a caused by surgery, or acid reflux disease.

Advantages of a gastrostomy over a nasogastric tube include a greater ability to provide food and calories and less chance of the feeding tube coming out. Moreover, a feeding tube is easier to replace than a nasogastric tube. A gastrostomy site is also less conspicuous than a nasogastric site. However, a gastrostomy is more likely to malfunction or leak. It is also more likely to cause infection or irritation of the patient's skin.

In a gastrostomy procedure, an opening or stoma is formed in the patient's abdomen and a feeding tube is installed with a first end protruding through the stoma and a second end in communication with the stomach. Gastrostomy tubes are typically used for patients who require enteral nutrition for more than thirty days. When the tube is first placed in the patient's stomach it is secured with stitches that extend through the skin and around the tube. This helps the tube stay in place until the gastrostomy tract is healed; healing takes about three weeks. After the initial healing, a natural tract develops between the stomach and skin. During this time, gauze is placed around the tube to absorb any drainage from the site. Gauze, however, binds to the skin and as a result the patient experiences pain with each replacement of gauze.

After the gastrostomy tract is healed, the feeding tube remains securely in the patient's stomach. A detent means in the form of a raised annular protuberance or bumper is positioned at an inner end of the tube inside the stomach. An inflated balloon may also be attached to the feeding tube inside the stomach to hold said feeding tube in place. A flange provided in the form of a plastic piece circumscribes the tube outside the patient's body. This configuration keeps the feeding tube from sliding in and out of the opening. The flange is formed integrally with the tube or is securely attached thereto so that there is no relative movement between the tube and the flange. The tube is able to move in and out of the patient's stomach just slightly. The flange fits snugly against the skin, but it does not bear thereagainst, i.e., it does not apply pressure thereto.

The site of the gastrostomy is susceptible to infection and leakage, particularly during the initial stages of healing. Gastric fluids may leak through the space between the outside of the tube and the stoma. Gauze is typically used to provide a dressing; it is attached to the skin with adhesive tape. Both the gauze and the tape become stuck to the skin so that changing the gauze is painful to the patient.

Hydrophilic foam dressings have developed that are effective in the treatment of highly exuding wounds such as skin graft donor sites, venous leg ulcers, and pressure ulcers. Foam dressings for a gastrostomy patient promote a sterile environment while absorbing excess fluids to prevent the skin from becoming too moist. Hydrophilic foam dressing allows a patient to maintain longer intervals between dressing changes.

Although hydrophilic dressings have been shown to form an effective bacterial barrier on the skin of a gastrostomy patient, these dressings are typically adhered to the skin with tape or other similar adhesive. Upon removal of the dressing, the dressing may adhere to the skin and cause discomfort to the patient. Disturbance of the site of the stoma can also introduce bacteria into the wound.

The hydrophilic devices and other medical appliances that have been developed to absorb bodily fluids exuding around a protruding tube are not available to the general public. They are medical-appliances used in hospitals by medical personnel. As is typical with hospital medical appliances, the devices of the prior art are used once and discarded. Thus, it would be desirable if a less wasteful alternative could be found.

U.S. Pat. No. 4,699,616 to Nowak et al. discloses a catheter retention device. It includes a core formed of thermoplastic foam for cushioning purposes but not for absorptive purposes. Accordingly, a material that presents a barrier to liquid covers the foam core.

Another cannula-anchoring device formed of non-absorptive materials is disclosed in U.S. Pat. No. 5,364,367 to Banks.

Gisselberg et al., in U.S. Pat. No. 5,569,207, disclose a dressing applied around a catheter. The dressing includes a lip that extends into an exit site so that part of the dressing extends a short distance into the subcutaneous tissue along the catheter tract in the patient. The edges of the dressing may be secured to the skin of the patient by using a gauze tape or other type of adhesive material. In the alternative, the dressing is secured to the catheter and both items are moved into their final positions together. The side of the dressing away from the patient's skin is formed of a liquid-impermeable barrier. Thus, the dressing is not reversible.

It would also be desirable if a less wasteful alternative could be used in a home environment.

When a patient is sent home, the caregiver is simply instructed to keep gauze on the wound and to change the gauze frequently. Accordingly, a suitable device that could be used in a non-hospital environment is highly desirable.

In summary, the needed improvements include a device that does not adhere to the patient's skin upon removal of the dressing, that can easily be used in a home environment with a gastrostomy feeding tube to absorb gastric fluids, and which is inexpensive and re-useable.

However, in view of the prior art considered as a whole at the time the present invention was made, it was not obvious to those of ordinary skill in the pertinent art how the identified needs could be fulfilled.

SUMMARY OF INVENTION

The long-standing but heretofore unfulfilled need for a feeding tube skin guard that can be used at home in a non-hospital environment, which can be replaced painlessly, and which can be re-washed and re-used, is now provided in the form of a new, useful and non-obvious device.

The novel device for absorbing liquids and protecting a patient's skin when a feeding tube is in use includes a disc-shaped member having a flexible and resilient construction. A central opening having a diameter about equal to a diameter of the feeding tube is formed in the disc-shaped member and is adapted to receive the feeding tube. A radial cut is formed in the disc-shaped member, extending from the central opening to an outer peripheral edge of the disc-shaped member.

A first releasable fastening means is mounted to a first side of the disc-shaped member near the radial cut and near the peripheral edge. The first releasable fastening means is also disposed on a first side of the radial cut.

A second releasable fastening means is mounted to a second side of the disc-shaped member near the radial cut and near the peripheral edge. The second releasable fastening means is also disposed on a second side of the radial cut.

The disc-shaped member has a top wall, a bottom wall, and a hydrophilic core of predetermined thickness disposed in sandwiched relation between the top and bottom walls.

The top and bottom walls are formed of a preselected open mesh material so that fluids drawn to the hydrophilic core by capillary action may pass through the open mesh material. The open mesh material is formed of a material that does not adhere to the patient's skin so that the device may be replaced as needed without causing discomfort to the patient.

In a preferred embodiment, the preselected open mesh material is nylon and the thickness of the hydrophilic core is about 1.0 cm. The preferred material for the hydrophilic core is hydrophilic polyurethane foam.

The top wall and the bottom wall are preferably sewn to one another along their respective outer peripheral edges and inner peripheral edges to envelope the hydrophilic core.

In a preferred embodiment, a hook and loop fastening means releasably secures the opposed free ends to one another.

An important object of the present invention is to provide an improved hydrophilic dressing device, for use with feeding tubes, that absorbs fluids and prevents skin irritation caused by the continuous drainage of stomach secretions onto a patient's skin.

Another object is to provide a means for attaching the hydrophilic dressing device in its proper, functional location without placing gauze or adhesive on the patient's skin so that the hydrophilic dressing device may be painlessly replaced as needed.

Another object is to provide a hydrophilic dressing device suitable for use in a non-hospital environment and which can be washed and re-used.

These and other important objects, advantages, and features of the invention will become clear as this description proceeds.

It is to be understood that both the foregoing general description and the following detailed description are explanatory and are not restrictive of the invention as claimed. The accompanying drawings, which are incorporated in and constitute part of the specification, illustrate embodiments of the present invention and together with the general description, serve to explain principles of the present invention.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

Detailed Description

Figure 1:
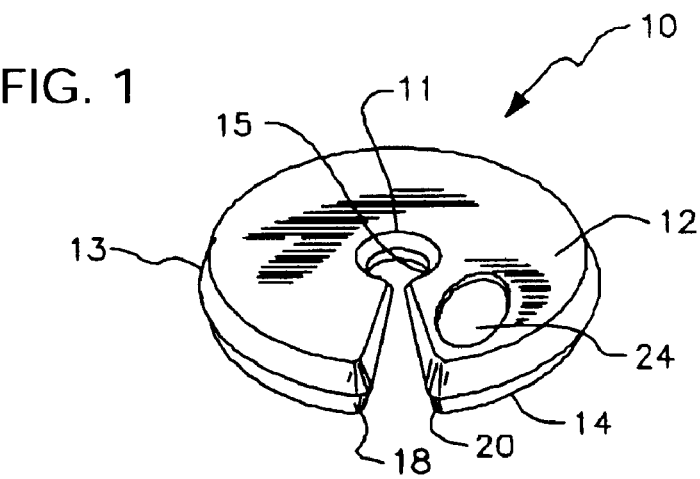
FIG. 1 is a top perspective view of the novel hydrophilic dressing device of the present invention in an open position.
Figure 2:
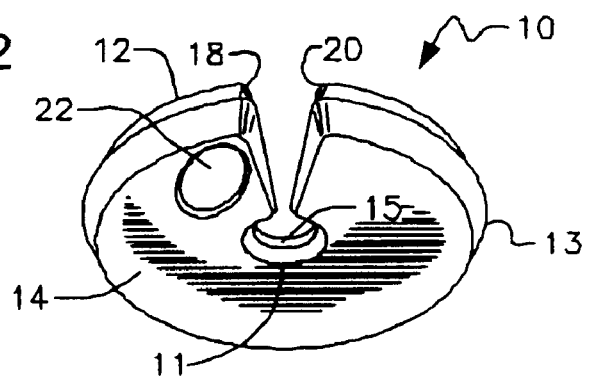
FIG. 2 is a bottom perspective view thereof.

Referring now to FIGS. 1 and 2, it will there be seen that the reference numeral 10 denotes a first embodiment of the novel hydrophilic dressing device as a whole. Device 10 will be known commercially as the Stout TM feeding tube skin guard.

In this first embodiment, device 10 includes a first or top disc-shaped wall 12, a second or bottom disc-shaped wall 14 that overlies the patient's skin, and a hydrophilic core 16, not depicted in FIGS. 1 and 2. Hydrophilic core 16, also of disc-shaped configuration, is preferably about one centimeter in thickness and is sandwiched between disc-shaped walls 12 and 14. The preferred material for hydrophilic layer 16 is hydrophilic polyurethane foam.

Device 10 further includes an inner peripheral seam 11 and an outer peripheral seam 13. The inner peripheral edges of first disc-shaped wall 12 and second disc-shaped wall 14 are sewn together about their periphery to form said inner peripheral seam 11. The outer peripheral edges of first disc-shaped wall 12 and second disc-shaped wall 14 are sewn together about their periphery to form said outer peripheral seam 13. Peripheral seams 11 and 13 thereby compress the annular peripheral edge of the sandwiched hydrophilic layer 16, as perhaps best depicted in FIG. 5 which shows the compression caused by inner peripheral seam 11.

Second disc-shaped wall 14 is preferably made of nylon or equivalent material because such material, unlike gauze, does not adhere to skin. Moreover, nylon or its equivalent is an open mesh material so that hydrophilic core 16 may absorb fluids through the openings. First disc-shaped wall 12 is also preferably formed of nylon, so that either first disc-shaped wall 12 or second disc-shaped wall 14 may abut the patient's skin in this embodiment. Accordingly, device 10 is reversible and the care-giver need not be concerned with orienting a particular side of the device so that it abuts the patient's skin. Both nylon and foam 16 have a flexible and resilient construction.

Foam 16 at the core of device 10 absorbs leaking bodily fluids from the stoma by capillary action. Such material 16 is sufficiently hydrophilic to enable device 10 to be changed and washed every eight to twelve hours or per required need.

Since device 10 is made of nylon and hydrophilic polyurethane foam, it may be washed in a conventional residential washing machine, dried in a conventional residential drier, and re-used.

Figure 3:
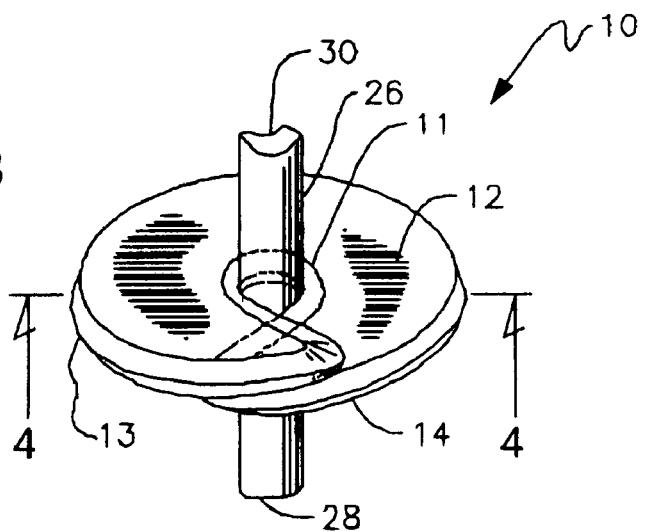
FIG. 3 is a perspective view of the novel hydrophilic device in a closed position where it is operatively attached to a catheter.

Device 10 has a disc-shaped structure so that it fits snugly about a feeding tube. It is cut along a radial line that extends from central opening 15 to the outer peripheral edge of disc-shaped member 10 so that its opposed ends may be momentarily spaced apart from one another when the device is fitted about a feeding tube. The opposed ends are then releasably secured to one another so that the device extends completely around the tube as depicted in FIG. 3. The diameter of central opening 15 is about equal to the diameter of a feeding tube.

The opposed free ends are denoted 18 and 20 in FIGS. 1 and 2 where they are depicted slightly spaced apart from one another. Opposed free ends 18 and 20 are depicted in overlapping relation to one another in FIG. 3. Note that central opening 15 grips the feeding tube when opposed free ends 18, 20 are secured to one another. The strength of the grip is sufficient to prevent travel of disc-shaped member 10 along the extent of the feeding tube when the disc-shaped member 10 is in abutting relation to a patient's skin. The grip is sufficiently weak, however, to enable a care-giver to slide disc-shaped member 10 along said feeding tube into abutting relation to the patient's skin. The grip is sufficiently strong so that there is no need to use gauze tape or any other adhesive to hold disc-shaped member 10 in its functional position against the skin.

Any means for releasably securing opposed free ends 18, 20 to one another is within the scope of this invention. For example, opposed free ends 18, 20 could be releasably joined to one another with strings, buckles, hooks any other suitable fastening means. The preferred fastening means employs hook and loop fabric pieces where a hook fabric piece 22 is secured to second disc-shaped wall 14 in the manner depicted in FIG. 2 and a loop fabric piece 24 is secured to first disc-shaped wall 12 as depicted in FIG. 1. Hook fabric piece 22 is placed in overlying relation to loop piece 24 to secure device 10 as best understood by comparing FIGS. 1 and 2 with FIG. 3. This facilitates the interlocking of opposed ends 18, 20 to one another in tightly fitting, circumscribing relation to feeding tube 26.

Feeding tube 26 (FIG. 3), also known as a gastrostomy tube as mentioned above, is surgically placed partially inside a patient's abdomen with inner end 28 in communication with the patient's stomach. Nutrients are introduced though outer end 30 of the tube. No part of device 10 enters into the exit site and no part of device 10 is adhered to the patient's skin.

Figure 4:
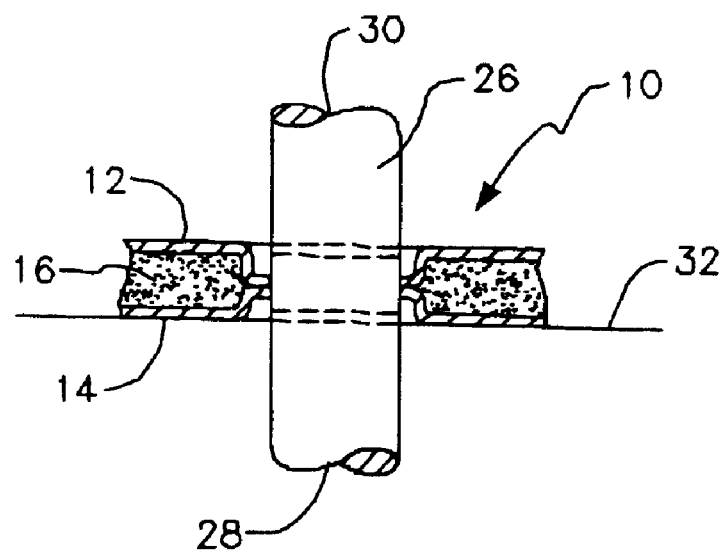
FIG. 4 is a cross sectional view taken along line 4—4 of FIG. 3.

Device 10 is positioned adjacent an opening such as a stoma (not shown) that breaches the patient's skin 32 as indicated in FIG. 4. No adhesive is required between second disc-shaped wall 14 and skin 32 to maintain device 10 in the proper location.

Figure 5:
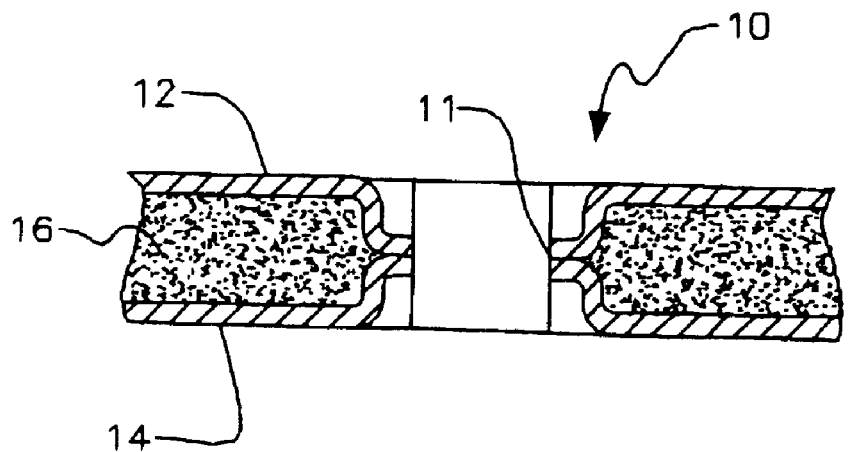
FIG. 5 is an enlarged cross sectional view thereof.

FIG. 5 provides a more detailed view of the first embodiment of device 10. Hydrophilic material 16 is sandwiched between first disc-shaped wall 12 and second disc-shaped wall 14 as aforesaid.

Device 10 is inexpensive to manufacture and therefore is affordable by consumers. It may be washed and re-used, making it even more affordable. Its elegant structure makes it easy to use. Perhaps most importantly, its nylon cover never sticks to the patient's skin. Since both walls 12 and 14 are formed of nylon, the device is reversible. Moreover, the open mesh structure of the nylon cover does not interfere with the absorbance function of foam core 16. Thus, the discomfort associated with gauze and other unacceptable absorption means is not experienced when device 10 is used.

It will be thus seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A device for absorbing liquids and protecting a patient's skin when a feeding tube is in use, comprising:

a disc-shaped member having a flexible and resilient construction;

a central opening formed in said disc-shaped member, said central opening having a diameter about equal to a diameter of a feeding tube and said central opening adapted to receive said feeding tube;

a radial cut formed in said disc-shaped member, said radial cut extending from said central opening to an outer peripheral edge of said disc-shaped member;

said disc-shaped member having a top wall, a bottom wall, and a hydrophilic core of predetermined thickness disposed in sandwiched relation between said top and bottom walls;

a first releasable fastening means mounted to said top wall of said disc-shaped member near said radial cut and near said outer peripheral edge, said first releasable fastening means being disposed on a first side of said radial cut;

a second releasable fastening means mounted to said bottom wall of said disc-shaped member near said radial cut and near said outer peripheral edge, said second releasable fastening means being disposed on a second side of said radial cut;

said central opening gripping said feeding tube when said first releasable fastening means is in releasable engagement with said second releasable fastening means, said gripping being sufficiently strong to hold said disc-shaped member against displacement along the extent of said feeding tube when said disc-shaped member is disposed in abutting relation to the patient's skin and said gripping being sufficiently weak to enable sliding of said disc-shaped member along said feeding tube into abutting relation to said patient's skin;

said top and bottom walls being formed of a preselected open mesh material so that fluids drawn to said hydrophilic core by capillary action pass through said open mesh material; and said preselected open mesh material being formed of a material that does not adhere to said patient's skin so that the device may be replaced as needed without causing discomfort to the patient and so that the device is reversible.

2. The device of claim 1, wherein said preselected open mesh material is nylon.

3. The device of claim 1, wherein said predetermined thickness of said hydrophilic core is about 1.0 cm.

4. The device of claim 1, wherein said hydrophilic core is formed of hydrophilic polyurethane foam.

5. The device of claim 1, wherein the first and second releasable fastening means are formed of complementary hook and loop fastening members.

* * * * *